(12) United States Patent
Gobin et al.

(10) Patent No.: US 8,663,676 B2
(45) Date of Patent: Mar. 4, 2014

(54) DEHYDRATED GRANULAR COMPOSITION AND BIOMEDICAL APPLICATIONS THEREOF

(75) Inventors: Chantal Gobin, Vigneux de Bretagne (FR); Xavier Bourges, Nogneneins (FR)

(73) Assignee: Biomatlante, Vigneux de Bretagne (FR)

( * ) Notice: Subject to any disclaimer, the term of this patent is extended or adjusted under 35 U.S.C. 154(b) by 572 days.

(21) Appl. No.: 12/529,489

(22) PCT Filed: Feb. 29, 2008

(86) PCT No.: PCT/EP2008/052488
§ 371 (c)(1),
(2), (4) Date: Oct. 27, 2009

(87) PCT Pub. No.: WO2008/107384
PCT Pub. Date: Sep. 12, 2008

(65) Prior Publication Data
US 2010/0034751 A1    Feb. 11, 2010

(30) Foreign Application Priority Data
Mar. 1, 2007    (FR) .................................... 07 53590

(51) Int. Cl.
*A61F 2/00*    (2006.01)

(52) U.S. Cl.
USPC ........................................ 424/426; 424/489

(58) Field of Classification Search
USPC ....................................................... 424/426
See application file for complete search history.

(56) References Cited

U.S. PATENT DOCUMENTS

| | | | |
|---|---|---|---|
| 4,781,925 A * | 11/1988 | Michelucci et al. | 424/465 |
| 5,717,006 A | 2/1998 | Daculsi et al. | |
| 6,001,394 A | 12/1999 | Daculsi et al. | |
| 6,187,046 B1 * | 2/2001 | Yamamoto et al. | 623/16.11 |
| 6,777,001 B1 | 8/2004 | Umezu et al. | |
| 2010/0068243 A1 * | 3/2010 | Khairoun et al. | 424/426 |

FOREIGN PATENT DOCUMENTS

| | | |
|---|---|---|
| EP | 0 692 986 B1 | 7/2000 |
| FR | 2 737 663 A1 | 2/1997 |
| JP | 3-11006 A | 1/1991 |
| WO | WO-00/07639 A1 | 2/2000 |
| WO | WO-03/024211 A2 | 3/2003 |

OTHER PUBLICATIONS

Pontier et al (Energetic yields in apatitic calcium phosphate compression: influence of the Ca/P molar ratio. Polymer International, vol. 52, No. 4, Apr. 2003, pp. 625-628(4)).*

Daculsi et al., "Macroporous Biphasic Calcium Phosphate Efficiency in Mastoid Cavity Obliteration: Experimental and Clinical Findings", Annals of Otology, Rhinology & Laryngology, vol. 101, No. 8 (Aug. 1992) pp. 669-674.

Daculsi et al., "Macroporous Calcium Phosphate Ceramic for Long Bone Surgery in Humans and Dogs. Clinical and Histological Study", Journal of Biomedical Materials Research, vol. 24 (1990) pp. 379-396.

Passuti et al., "Macroporous Calcium Phosphate Ceramic Performance in Human Spine Fusion", Clinical Orthopaedics, vol. 248 (Nov. 1989) pp. 169-176.

* cited by examiner

*Primary Examiner* — Jake Vu
(74) *Attorney, Agent, or Firm* — Birch, Stewart, Kolasch & Birch, LLP

(57) ABSTRACT

The invention relates to a granular composition for a biomaterial, that comprises from 0.1 to 5 wt % of at least one polymer derived from cellulose, 75 to 99.9 wt % of a mineral phase containing hydroxyapatite and/or β tricalcic phosphate, and 0 to 10 wt % of water, preferably 0 to 7 wt % of water, more preferably 0 to 5 wt % of water, and even more preferably approximately 5 wt % of water.

19 Claims, No Drawings

DEHYDRATED GRANULAR COMPOSITION AND BIOMEDICAL APPLICATIONS THEREOF

The present invention relates to a novel composition in a dry or quasi-dry form which may be hydrated in order to form a filler biomaterial which is injectable and usable in vertebroplasty, femoroplasty and mini-invasive surgery.

Bone substitutes based on calcium phosphate particles and on a biological adhesive are known from the state of the art.

Thus, G. Daculsi et al., have described in *Ann. Oto. Rhino. Laryngol.* 101: 1992, the effectiveness of a microporous biphasic composition of calcium phosphate for improving the mastoidal cavity.

The same authors have also reported the effectiveness of a macroporous composition of biphasic calcium phosphate for the surgical preparation of long bones (*Journal of Biomedical Material Research* Vol. 24, 379-396) and in vertebral arthrodeses (*Clinical Orthopaedics and Related Research* 1989, 248, 169-175).

On the one hand, patent JP 3 011 006 describes a cement for hard tissues comprising a mineral phase consisting of at least 60% of alpha tricalcium phosphate and of hydroxyapatite and/or calcium monophosphate, and a liquid phase comprising carboxymethylcellulose.

Such a composition however has the drawback, because of the too high solubility of alpha tricalcium phosphate, of not being sufficient stable in order to allow a hard tissue resorption/substitution process. Further, such a composition is capable of generating detrimental inflammatory processes. This mixture is a calcium ionomer unsuitable for injection after a few minutes, by hardening of the mixture as soon as it is formed. This combination has dual instability, volumetric contraction with salting out of water after several days, and especially a drop in the viscosity after sterilization of the mixture in the autoclave.

Patent EP 0 692 986 describes a "ready-for-use" injectable composition of resorption/substitution biomaterial for dental, bone and osteo-articular supporting tissues consisting of 40-75% by weight of a mineral phase comprising either a mixture of β tricalcium phosphate (A) and of hydroxyapatite (B) in a ratio AB comprised between 1/4 and 7/3, or of calcium titanium phosphate ($Ca(Ti)_4(PO_4)_6$) and of 60-25% by weight of a liquid phase comprising an aqueous solution of a polymer derived from cellulose. Unfortunately, these gels have a short life time, making their preservation delicate. Indeed, after a resting period from one to two weeks, demixing of these compositions has-been observed.

The object of the present invention is to avoid such stability problems by providing a sterile composition in dry or quasi-dry form which may be hydrated extemporaneously in order to form an injectable gel.

More specifically, the composition according to the invention is in granular form and comprises by weight 0.1-5% of at least one polymer derived from cellulose, 75-99.9% of a mineral phase comprising hydroxyapatite and/or β tricalcium phosphate and 0-10% of water, preferably 0-7% of water, more preferentially 0-5% of water, still more preferentially about 5% of water.

The composition according to the invention therefore comprises up to about 10% of water, and advantageously about 5% of water.

By a polymer derived from cellulose is meant a hydrophilic and water-soluble polymer of cellulose, the hydroxyl groups of which have been replaced by various substituents.

The polymer derived from cellulose may be selected from the group comprising hydroxypropylmethyl cellulose, methyl cellulose, hydroxyethyl cellulose and carboxymethyl cellulose.

According to a particularly advantageous embodiment of the invention, the polymer derived from cellulose is hydroxypropylmethyl cellulose (HPMC).

Advantageously, the hydroxyapatite/β tricalcium phosphate weight ratio in the mineral phase, is comprised between 10/90 and 90/10, still more advantageously comprised between 20/80 and 80/20.

According to a particularly advantageous embodiment of the invention, the mineral phase according to the invention comprises by weight 60% of hydroxyapatite and 40% of β tricalcium phosphate.

Still advantageously, hydroxyapatite and β tricalcium phosphate have a grain size comprised between 40 and 200 µm.

An additional advantage of the invention is provided by the fact that the composition may be hydrated extemporaneously with various aqueous solutions.

The object of the invention is also therefore the use of a granular composition as described earlier for making a hydrogel extemporaneously, characterized in that it consists of mixing the granular composition according to the invention, with a liquid selected from the group comprising water, saline, plasma or biological fluids, either containing or not products from tissue engineering, PRP (Platelet-Rich Plasma), bone marrow, or further contrast agent solutions for nuclear magnetic resonance imaging (MRI) or radio-opaque agent solutions for X-ray imaging.

The compositions according to the invention have a great utility for new increasingly practiced surgical techniques, such as vertebroplasty or kyphoplasty. These operations require biomaterials of radio-opaque nature (either permanently or not depending on the cases). They are indeed performed on more or less fractured vertebrae and escape of material out of the vertebrae may be critical, giving rise to neurological and vascular complications which may cause death. It is therefore absolutely necessary that the surgeon be able to observe the amount of injected product, its dispersion into the vertebra, and especially check whether the material actually remains inside the latter.

The volume of liquid should not be larger than what the granular composition may absorb in order to avoid demixing of the powder in vivo.

The amount of liquid added to the granular composition is adjusted in order to obtain an injectable gel.

Because of the large variety of solutions which may be added to the granular composition, the amount of liquid is expressed as a volume (mL) added to a weight (g) of granular composition.

Preferentially, the proportion of liquid relatively to the proportion of granular composition is comprised between 35 mL of liquid for 65 g of granular composition and 55 mL of liquid for 45 g of granular composition, more preferentially between 40 mL of liquid for 60 g of granular composition and 50 mL of liquid for 50 g of granular composition, still more preferentially equal to 45 mL of liquid for 55 g of granular composition.

According to the invention, the radio-opaque agents for medical X-ray imaging may advantageously be ionic or non-ionic, iodinated compounds, such as Iomeron® or Iopamidol®. These iodinated solutions make the gel totally radio-opaque and they may therefore be detected by X-ray radiography.

The radio-opaque agents present in the injected gel have the additional advantage of disappearing over time, so that it is possible to evaluate the effectiveness of the bone reconstruction.

Further, bone substitutes obtained after hydration of the compositions according to the invention with a iodinated solution, have exceptional rheological properties. They form viscous products with a thick structure in the form of injectable paste (of the toothpaste type).

Contrast agents for medical imaging by nuclear magnetic resonance may be used, notably in the case of allergy of the patient to iodine. Advantageously, such contrast agents contain gadolinium(III), such as the product ProHance® for example.

The hydrogels containing a contrast agent for MRI may be observed after injection. The surgeon may thus verify their proper implantation. The contrast agents are then rapidly eliminated from the body of the patient.

The object of the invention is also novel gels obtained by hydration of dry compositions, notably gels containing contrast agents.

The object of the invention is also the use of these hydrogels as a bone substitute.

The object of the invention is also the method for preparing the compositions described earlier. Such a method comprises the following successive steps:
  preparation of a homogeneous mixture comprising the mineral phase and the aqueous solution of polymer derived from cellulose;
  dehydration of the mixture, for example by means of a freeze drier or an oven;
  optional deagglomeration of the dehydrated product, for example on a sieve of 300 µm;
  sterilization of the dehydrated product, for example in an autoclave.

Advantageously, the sterilization temperature is 121° C.

The invention will now be illustrated in a non-limiting way by the following examples.

Exemplary Composition 1:

A bone substitute was thus prepared:

30 g of hydroxypropylmethyl cellulose (HPMC) of the E4M type were dissolved in 970 g of saline solution with a mechanical stirrer for 24 hours.

Granules of calcium phosphate ceramic MBCP® (Biomatlante), containing by weight 60% of hydroxyapatite and 40% of β tricalcium phosphate with a size comprised between 80 and 200 µm were prepared by wet sieving.

The granules were added to the HPMC solution in the following weight proportions: 45% of HPMC solution and 55% of granules. The mixing was carried out with a mechanical kneader.

The bone substitute was then freeze-dried up to a humidity level of less than 5%, and 5.5 g of the freeze-dried product were positioned in 12 mL polycarbonate syringes having a system for letting through steam. The syringes containing the bone substitute were sterilized in the autoclave at 121° C. for 30 minutes.

After sterilization, the bone substitute was reconstituted by 4.5 mL of radio-opaque solution Iomeron® 250. The radio-opaque product was picked up by means of a 12 mL syringe connected to the syringe containing the freeze-dried bone substitute by means of female-female Luer lock connector. The contrast product was injected into the inside of the syringe containing the bone substitute and the whole was passed several times from one syringe to the other in order to homogenize the final product. The bone substitute containing the contrast product is then ready for use.

It was checked under viewing that the radio-opacity of the thereby prepared product was sufficient and that the fact of adding the contrast product did not change biocompatibility, neither did it influence bone regrowth.

Verification in vivo of the innocuousness of the hydrated gel in New Zealand rabbits:

A bone substitute was prepared by hydrating with sterile water a dry composition containing 94.2% by weight of biphasic calcium phosphate granules consisting of 60% of hydroxyapatite and 40% of β tricalcium phosphate with a size comprised between 80 and 200 µm, 2.3% of hydroxypropylmethyl cellulose and 3.5% of water.

A bone substitute containing Iomeron® was also prepared as described earlier.

Operating Procedure

The animals having participated in the study were all mature. The retained injection site was the femoral endomedullar site.

Each animal was operated on both femurs. The operated limb was shaved a few minutes before the operation.

The anaesthetic procedure was the following:

15 minutes before the operation, intramuscular injection of 250 mg of ketamine hydrochloride.

1-2 minutes before the operation, local and intramuscular anaesthesia of the knee, with a mixture of 1% lidocaine hydrochloride (Xylocaine adrenaline, Astra France, Nanterre) in respective proportions of 2/3-1/3.

The operation was carried out under strict asepsy conditions.

The anaesthetized animal is placed in dorsal decubitus, with the four limbs fastened.

A block is slipped under the knee on the operated side in order to maintain a flexure of about 30° of this knee. The operating site is then isolated by a pierced sterile field.

The steps are the following:
Internal parapatellar cutaneous incision of about 3 cm.
Internal patellar wing and articular capsule incision.
Drilling with a 6 mm diameter bit, a channel in the trochlear throat.
Haemostasis by means of a sterile compress.
Slow injection of the prepared bone substitutes (with or without Iomeron®), as described earlier.
An MBCP plug with a diameter of 6.5 mm is then positioned in order to prevent bone substitute from flowing out of the implantation site.
Closure in a single plane of the capsule and of the patellar wing by a sealed vicryl suture.
Skin closure with a sealed vicryl suture.
Placing a disinfecting betadine gel on the suture.
Placing an elastoplast band.

No antibiotherapy was used preoperatively or postoperatively.

All the animals were sacrificed 6 weeks after implantation by a lethal intravenous injection of 0.25 g of sodium thiopental (Nesdonal, Spécia Rhone Poulenc Paris).

The implants were recovered and were treated in order to include them in GMA resin. Various analyses were conducted.

Results of Histological Analyses

Quantitative analyses allowed determination of bone regrowth rate, resorption of the material and quality of the newly-formed bone. The techniques used were microtomodensitometry, polarized microscopy, and electronic scanning microscopy.

No difference in bone regrowth is observable between dry MBCP gel reconstituted with sterile water or with Iomeron®.

Innocuousness of both products was confirmed and no foreign body rejection reaction was observed.

RECONSTRUCTION EXAMPLE 2

A freeze-dried MBCP/HPMC injectable bone substitute, identical with the previous Example 1, was prepared in 1 mL syringes (0.55 g of freeze-dried gel).

After sterilization, the bone substitute was reconstituted with 4 types of solutions of biological origin:

| | | |
|---|---|---|
| i) | Cell culture plasma, bone serum | 0.45 mL |
| ii) | Human serum obtained by centrifugation and platelet concentrate (PRP) | 0.45 mL |
| iii) | Blood (rabbit) separated on Ficoll (without a red line) | 0.50 mL |
| iv) | Total bone marrow (rabbit) | 0.50 mL |

The 4 solutions were prepared in 1 mL syringes with Luer lock. The syringe containing the freeze-dried MBCP gel was connected to the syringe containing the biological fluid or cell derivative, and its contents were injected into the bone substitute. The whole was passed several times from one syringe to the other in order to homogenize the final product.

Injectability/extrusion was observed. It was noted that reconstitution of the freeze-dried MBCP gel with biological fluids, either containing or not figurative elements such as platelets or cells, is possible and they impart to the bone substitute sufficient properties for extrusion and filling of bone or osteoarticular defects.

The invention claimed is:

1. A granular composition for a biomaterial capable of being re-hydrated extemporaneously with an aqueous solution to form a hydrogel, comprising by weight
    0.1 to 5% of at least one polymer derived from cellulose,
    75 to 99.9% of a mineral phase consisting of hydroxyapatite and/or β tricalcium phosphate and
    0 to 10% of water.

2. The composition according to claim 1, wherein the polymer derived from cellulose is selected from the group comprising hydroxypropylmethyl cellulose, methyl cellulose, hydroxyethyl cellulose, carboxymethyl cellulose.

3. The composition according to any of the preceding claims, wherein the hydroxyapatite/β tricalcium phosphate weight ratio in the mineral phase is comprised between 10/90 and 90/10.

4. The composition according to claim 1, wherein the hydroxyapatite and β tricalcium phosphate have a grain size comprised between 40 and 200 μm.

5. An extemporaneous process of preparation of a hydrogel, which comprises
    mixing the granular composition according to claim 1 with a liquid selected from the group consisting of water, saline, blood plasma or PRPs, bone marrow, derivatives from tissue engineering, contrast agent solutions for nuclear magnetic resonance imaging and radio-opaque compound solutions for X-ray imaging.

6. The process according to claim 5, the liquid proportion relatively to the granular composition proportion, is comprised between 35 mL of liquid for 65 g of granular composition and 55 mL of liquid for 45 g of granular composition.

7. The process according to claim 5, wherein the contrast agents for medical X-ray imaging are ionic or non-ionic iodinated compounds.

8. The process according to claim 5, wherein the contrast agents for medical nuclear magnetic resonance imaging contain gadolinium(III).

9. A hydrogel obtained by the process according to claim 5.

10. A method thr making a composition according to claim 1, which comprises the following successive steps:
    preparing an aqueous homogenous mixture comprising the mineral phase and at least one polymer derived from cellulose;
    dehydrating the mixture;
    optionally deagglomerizing the dehydrated product;
    sterilizing the dehydrated product.

11. The composition according to claim 1, wherein it comprises by weight 0 to 7% of water.

12. The composition according to claim 1, wherein it comprises by weight 0 to 5% of water.

13. The composition according to claim 1, wherein it comprises by weight about 5% of water.

14. The composition according to claim 2, wherein the polymer derived from cellulose is hydroxypropylmethyl cellulose.

15. The composition according to claim 3, wherein the hydroxyapatite/β tricalcium phosphate weight ratio in the mineral phase is comprised between 20/80 and 80/20.

16. The composition according to claim 3, wherein the hydroxyapatite/β tricalcium phosphate weight ratio in the mineral phase is about 60/40.

17. The process according to claim 6, wherein the liquid proportion relatively to the granular composition proportion, is comprised between 40 mL of liquid for 60 g of granular composition and 50 mL of liquid for 50 g of granular composition.

18. The process according to claim 6, wherein the liquid proportion relatively to the granular composition proportion, is equal to 45 mL of liquid for 55 g of granular composition.

19. A granular composition for a biomaterial capable of being re-hydrated extemporaneously with an aqueous solution to form a hydrogel, consisting of by weight
    0.1 to 5% of at least one polymer derived from cellulose,
    75 to 99.9% of a mineral phase consisting of hydroxyapatite and/or β tricalcium phosphate and
    0 to 10% of water.

* * * * *